United States Patent
Desfougeres et al.

(10) Patent No.: US 10,920,232 B2
(45) Date of Patent: Feb. 16, 2021

(54) OBTAINING HIGH-PERFORMANCE YEAST STRAINS FOR METABOLIZING ARABINOSE

(71) Applicant: LESAFFRE et COMPAGNIE, Paris (FR)

(72) Inventors: Thomas Desfougeres, Dissay (FR); Emilie Fritsch, London (GB); Georges Pignede, Marcq en Baroeul (FR); Christophe Rave, Lambersart (FR); Claire Thorel, Roncq (FR)

(73) Assignee: LESAFFRE et COMPAGNIE, Paris (FR)

( * ) Notice: Subject to any disclaimer, the term of this patent is extended or adjusted under 35 U.S.C. 154(b) by 0 days.

(21) Appl. No.: 16/475,845

(22) PCT Filed: Jan. 24, 2018

(86) PCT No.: PCT/EP2018/051708
§ 371 (c)(1),
(2) Date: Jul. 3, 2019

(87) PCT Pub. No.: WO2018/138135
PCT Pub. Date: Aug. 2, 2018

(65) Prior Publication Data
US 2019/0330645 A1 Oct. 31, 2019

(30) Foreign Application Priority Data

Jan. 24, 2017 (FR) .................................. 17 50550

(51) Int. Cl.
| | | |
|---|---|---|
| *C12N 15/81* | (2006.01) | |
| *C12N 1/16* | (2006.01) | |
| *C12N 1/22* | (2006.01) | |
| *C12P 7/10* | (2006.01) | |
| *C12R 1/865* | (2006.01) | |

(52) U.S. Cl.
CPC .............. *C12N 15/81* (2013.01); *C12N 1/16* (2013.01); *C12N 1/22* (2013.01); *C12P 7/10* (2013.01); *C12R 1/865* (2013.01); *C12N 2500/02* (2013.01); *C12N 2500/34* (2013.01)

(58) Field of Classification Search
None
See application file for complete search history.

(56) References Cited

U.S. PATENT DOCUMENTS

| | | | | |
|---|---|---|---|---|
| 8,445,243 | B2 * | 5/2013 | Matsushika | ............ C12N 15/81 435/161 |
| 9,441,249 | B2 * | 9/2016 | Kondo | ...................... C12N 1/14 |
| 10,100,320 | B2 * | 10/2018 | Klaassen | ................... C12P 7/40 |
| 2014/0206070 | A1 | 7/2014 | Boles et al. | |

FOREIGN PATENT DOCUMENTS

| | | |
|---|---|---|
| FR | 3035405 A1 | 10/2016 |
| WO | WO-2003/095627 A1 | 11/2003 |
| WO | WO-2008/041840 A1 | 4/2008 |
| WO | WO-2008/122354 A1 | 10/2008 |
| WO | WO-2009/112472 A2 | 9/2009 |
| WO | WO-2010/000464 A1 | 1/2010 |
| WO | WO-2011/080411 A1 | 7/2011 |
| WO | WO-2012/072793 A1 | 6/2012 |
| WO | WO-2012/143513 A2 | 10/2012 |
| WO | WO-2013/178915 A1 | 12/2013 |
| WO | WO-2013/178918 A1 | 12/2013 |
| WO | WO-2014/207087 A1 | 12/2014 |
| WO | WO-2015/121595 A1 | 8/2015 |

OTHER PUBLICATIONS

Wisselink et al., "Engineering of *Saccharomyces cerevisiae* for efficient anaerobic alcoholic fermentation of L-arabinose", Applied and Environmental Microbiology, 73(15): 4881-4891 (2007) (Year: 2007).*
Bellissimi et al., Effects of acetic acid on the kinetics of xylose fermentation by an engineered, xylose-isomerase-based *Saccharomyces cerevisiae* strain, *FEMS Yeast Res.* 9:358-64 (2009).
Garay-Arroyo et al., Three genes whose expression is induced by stress in *Saccharomyces cerevisiae*, *Yeast.* 15:879-92 (1999).
Gulati et al., Assessment of ethanol production options for corn products, *Bioresource Technol.* 58:253-64 (1996).
Hanko et al., Determination of carbohydrates, sugar alcohols, and glycols in cell cultures and fermentation broths using high-performance anion-exchange chromatography with pulsed amperometric detection, *Anal. Biochem.* 283:192-9 (2000).
International Search Report and Written Opinion, PCT/EP2018/051708 (dated Jul. 6, 2018).
Kovalevsky et al., Inhibition of D-xylose isomerase by polyols: atomic details by joint X-ray/neutron crystallography, *Acta. Crystallogr. D. Biol. Crystallogr.* 68:1201-6 (2012).
Madhavan et al., Bioconversion of lignocellulose-derived sugars to ethanol by engineered *Saccharomyces cerevisiae*, *Crit. Rev. Biotechnol.* 32:22-48 (2012).
Schadel et al., Hemicellulose concentration and composition in plant cell walls under extreme carbon source-sink imbalances, *Physiol. Plant.* 139:241-55 (2010).
Schell et al., Contaminant occurrence, identification and control in a pilot-scale corn fiber to ethanol conversion process, *Bioresour. Technol.* 98:2942-8 (2007).
Swinnen et al., Improvement of yeast tolerance to acetic acid through Haa1 transcription factor engineering: towards the underlying mechanisms, *Microb. Cell Fact.* 16:7 (2017).

(Continued)

*Primary Examiner* — Anand U Desai
(74) *Attorney, Agent, or Firm* — Marshall, Gerstein & Borun LLP

(57) ABSTRACT

The present invention relates to methods for obtaining yeast strains suitable for metabolizing arabinose, and to improved strains with good performance as regards their capacity to ferment arabinose as well as xylose and glucose, including in the presence of inhibitors such as acetic acid.

20 Claims, 5 Drawing Sheets

Specification includes a Sequence Listing.

(56) References Cited

OTHER PUBLICATIONS

Traff et al., Deletion of the GRE3 aldose reductase gene and its influence on xylose metabolism in recombinant strains of *Saccharomyces cerevisiae* expressing the xylA and XKS1 genes, *Appl. Environ. Microbiol.* 67:5668-74 (2001).
Wang et al., Improvement of L-arabinose fermentation by modifying the metabolic pathway and transport in *Saccharomyces cerevisiae*, *Biomed. Res. Int.* 2013:461204 (2013).
Wiedemann et al., Codon-optimized bacterial genes improve L-Arabinose fermentation in recombinant *Saccharomyces cerevisiae*, *Appl. Environ. Microbiol.* 74:2043-50 (2008), (Abstract only).
Wisselink et al., Engineering of *Saccharomyces cerevisiae* for efficient anaerobic alcoholic fermentation of L-arabinose, *Appl. Environ. Microbiol.* 73:4881-91 (2007), (Abstract only).
Wisselink et al., Novel evolutionary engineering approach for accelerated utilization of glucose, xylose, and arabinose mixtures by engineered *Saccharomyces cerevisiae* strains, *Appl. Environ. Microbiol.* 75:907-14 (2009).

\* cited by examiner

A/

B/

A/

B/

SEQUENCE LISTING

```
<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "araA-v-f-1"

<400> SEQUENCE: 1
atgattcaag ctaagaccc                                               19

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "araA-v-r-1"

<400> SEQUENCE: 2
```
atgtcaatct tgtcccatgg                                                        20

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "araB-v-f-1"

<400> SEQUENCE: 3
atggctattg ctattggttt                                                        20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "araB-v-r-2"

<400> SEQUENCE: 4
ccacaaaacg aacatagcgt                                                        20

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "araD-v-f-1"

<400> SEQUENCE: 5
atgttggaag acttgaagag                                                        20

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "araD-v-r-1"

<400> SEQUENCE: 6
tagaagtagt cagcgtgggt                                                        20

<210> SEQ ID NO 7
<211> LENGTH: 27
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "B6C2"

<400> SEQUENCE: 7
cctattgctg tttcctcttc aaagtac                                                27

```
<210> SEQ ID NO 8
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: "B13B1"

<400> SEQUENCE: 8
tagttgtcag tgcaatcctt c                                              21
```

OBTAINING HIGH-PERFORMANCE YEAST STRAINS FOR METABOLIZING ARABINOSE

CROSS REFERENCE TO RELATED APPLICATIONS AND INCORPORATION BY REFERENCE OF MATERIAL SUBMITTED ELECTRONICALLY

This application is a U.S. National Stage of International Application No. PCT/EP2018/051708, filed Jan. 24, 2018, which claims the benefit of French Patent Application No. FR-1750550 filed Jan. 24, 2017, the entire contents of each of which are fully incorporated herein by reference.

A Sequence Listing, which is a part of the present disclosure, is submitted concurrently with the specification as a text file. The name of the text file containing the Sequence Listing is "54366_Seqlisting.txt." The Sequence Listing was created on Jul. 2, 2019 and is 2,297 bytes in size. The subject matter of the Sequence Listing is incorporated herein in its entirety by reference.

FIELD OF THE INVENTION

The present invention relates to yeast strains able to metabolize arabinose, advantageously in combination with their ability to ferment xylose and glucose in the presence of inhibitors of these last two fermentations such as acetic acid in non-dissociated form.

More specifically, the present invention provides a process for the selection of strains able to metabolize arabinose and its improved strains, operating in their capacity to metabolize arabinose and also xylose, both types of pentoses recovered in lignocellulosic hydrosylates.

BACKGROUND OF THE INVENTION

Lignocellulose or plant biomass, mainly coming from agricultural and agro-industrial activity, is a complex substrate made of three main fractions which are cellulose, hemicellulose and lignin. This concerns recyclable waste used in the manufacture of ethanol, the demand for which continues to rise due, for example, to its use as a biofuel.

The method for producing ethanol from lignocellulose biomass consists of recovering as much of the sugars present in the cellulose and hemicellulose fractions as possible by hydrolysis and then transforming them into ethanol by fermentation.

As for the fermentation of the sugars present in this biomass, including both C6 sugars (hexoses) and C5 sugars (pentoses), anaerobic fermentation by yeasts is preferred, in particular using *Saccharomyces cerevisiae*, whose capability for fermenting glucose is well controlled and developed.

However, full attention is given to the fermentation of pentoses, in particular xylose, which can represent up to 25 to 40% of the total sugars contained in the lignocellulose biomass. Thus, yeast strains able to ferment glucose were modified to also be able to metabolize pentoses.

As an example, document WO 2010/000464 reports obtaining yeast strains able to ferment pentoses because of a bacterial gene coding for a xylose isomerase (XI) which converts xylose into xylulose which can be metabolized by the yeast.

It should be noted that in an alternative way, a pathway comprising a xylose reductase (XR or XYL1) generating xylitol and a xylitol dehydrogenase (XDH or XYL2) can also produce xylulose.

Thus, document WO 2012/072793 describes improved yeast strains combining exogenous genes coding a xylose isomerase and a xylitol dehydrogenase able to eliminate xylitol which proves to be an inhibitor of xylose isomerase. Such strains, in particular the strain deposited at the CNCM (Collection Nationale de Cultures de Microorganismes) on Oct. 5, 2011 under number I-4538, have improved yields and therefore proven industrial utility for the production of ethanol.

Another crucial problem was showing, in the lignocellulose hydrolysates, the presence of fermentation inhibitors; among them are furaldehydes (furfural and HMF), phenolic compounds and organic acids (acetic acid, levulinic acid, formic acid, etc.). The presence of high concentrations of acetic acid, over 5 g/kg (initial medium) and which can reach 10 g/kg, is intrinsically linked to the presence of acetyl groups covalently bonded to hemicellulose molecules.

Prior work has taken on the improvement of the resistance of the strains to the presence of acetic acid in the fermentation musts. Thus, document WO 2011/080411 reported obtaining yeast strains with improved resistance to acetic acid on glucose.

However, acetic acid is also an inhibitor of xylose fermentation. This inhibition is characterized by a reduction of the kinetics of the consumption of the xylose (Bellisimi et al., FEMS Yeast Res., 2009, 9:358-364), while on the glucose, this inhibition is reflected by a delay in the initiation of the fermentation, the kinetics subsequently remaining unchanged. It should be noted that in the presence of both glucose and xylose in the medium, yeast strains ferment glucose first because of catabolite repression.

Thus documents WO 2013/178915 and WO 2013/178918 describe methods for obtaining yeast strains able to metabolize pentoses, in particular xylose, and resistant to fermentation inhibitors, in particular acetic acid.

Strains even more improved, particularly in their ability to ferment glucose and xylose in the presence of acetic acid, are described in documents WO 2015/121595 and FR 3 035 405.

All this work is concentrated on xylose as the pentose of interest. Even if it is generally considered the primary pentose in hemicellulose, xylose is not the only one. It is thus possible to also find arabinose in plant structures (Saddler, 1993, Wallingford, Oxon, UK: CAB International), in a proportion sometimes greater than 40% (Schadel et al., 2010, Physiologia Plantarum 139, 241-255). In addition, the arabinose is found in bagasse (Hanko and Rohrer, 2000, Anal. Biochem. 283, 192-199) or in fibers from corn called "corn fibers" (Gulati et al., 1996, Bioresource Technology 58, 253-264).

Besides the obvious economic value of additional fermentation of arabinose, it is also noteworthy that residual arabinose may form a substrate of choice for the development of contaminant miroorganisms that can possibly convert it into organic acids that are inhibitors of the fermentation of glucose and xylose, as previously stated (Schell et al., 2007, Bioresour. Technol. 98, 2942-2948.

Numerous microorganisms have been described as able to metabolize arabinose as well in fungal microorganisms, particularly hemi-ascomycetes such as *Scheffersomyces stipitis*, basidiomycetes and filamentous fungi, as in bacteria such as *Erwinia chrysanthemi*, *Thermoanaerobacterium saccharolyticum*, *Escherichia coli*, *Zymomonas mobilis*, *Bacillus subtilis*, *Bacillus licheniformis* and *Lactobacillus plantarum*.

However, among the yeast strains that can be used industrially, notably those that can support ethanol titers as high as those tolerated by the *Saccharomyces cerevisiae* yeast, none is reported as able to ferment arabinose naturally.

Document WO 03/095627 has reported the possibility of obtaining strains of *S. cerevisiae* capable of growing on arabinose by transforming a laboratory strain by multicopy plasmids specifically bearing genes araA (coding an L-arabinose isomerase) of *B. subtilis*, araB (coding an L-ribulokinase advantageously mutated) and araD (coding an L-ribulose-5-P-4 epimerase) of *E. coli*. This document raises the issue openly of the possibility of obtaining a strain capable of co-fermenting xylose.

Document WO 2008/122354 describes strains of *S. cerevisiae* transformed using self-replicating vectors carrying the genes araA of *B. licheniformis*, araB (advantageously mutated) and araD of *E. coli*, advantageously codon-optimized, able to grow in an aerobiose or anaerobiose medium containing arabinose as the sole source of carbon. Transformants are selected by culture in a medium containing glucose as the carbon source.

Document WO 2008/041840 describes specific sequences of araA, araB and araD that give a yeast the ability to metabolize arabinose, in this case from *L. plantarum*. In practice, genes are introduced via plasmids into a laboratory of *S. cerevisiae* deleted for the aldose reductase gene GRE3, overexpressing pentose phosphates pathway (TAL, TKL1, RPE1 and RKI1) and expressing xylose fermentation pathway (XI or XylA and XKS1). According to the authors, a strain like this cannot grow directly on a medium containing arabinose, and preculture on a medium containing galactose is required. Additionally, the strains obtained from said cultures have lost their ability to metabolize xylose.

Document WO 2012/143513 reports the chromosomal integration of at least araA, araB and araD and XylA genes in a yeast species of the type *Saccharomyces* that, after culturing with the Sequential Batch Repeat method described in WO 2009/112472 in a medium containing 20 g/L of arabinose and 20 g/L of xylose, give it the ability to ferment glucose, xylose and arabinose. Mutations of different genes (SSY1, YJR154w, CEP3, GAL80, PMR1) were observed.

However, a need to obtain yeast strains able to metabolize arabinose showed up, in addition to their ability to ferment glucose and xylose even in the presence of acetic acid.

DESCRIPTION OF THE INVENTION

The present invention concerns the identification of new strains of yeast suitable for metabolizing at least arabinose, based on the contributions of the inventors in connection with various aspects:

highlighting the fact that introducing the arabinose metabolic pathway is necessary but insufficient to guarantee the effective metabolism of arabinose;

highlighting the possibility of directly selecting transformants having integrated the arabinose metabolization pathway onto a medium containing arabinose as the sole source of carbon;

highlighting the need for strict control of the production of polyol to ensure the efficient fermentation of arabinose;

highlighting that fermentation of xylose and arabinose can coexist in a stable environment;

perfecting a protocol for the selection of yeast strains able to improve fermentation of arabinose, xylose and glucose at the same time, including the fermentation of the two latter sugars in the presence of fermentation inhibitors such as acetic acid.

According to a first aspect, the present invention relates to a process for obtaining and/or selecting a yeast strain capable of metabolizing arabinose, comprising the following steps:

introduction of the pathway for metabolizing arabinose into a yeast strain;

selection of a strain able to express said pathway based on at least one of the following criteria:

a/ its ability to metabolize the arabinose present in a culture medium containing the aforesaid arabinose as the sole carbon source, and/or b/ low or even null aldose reductase activity.

According to a particular embodiment, said process comprises:

the chromosomal integration of araA, araB and araD genes, advantageously araA of *B. licheniformis*, araB and araD of *E. Coli*, in a yeast strain;

direct placement into culture of the transformed strains into a medium containing arabinose as the sole carbon source for the selection of strains able to metabolize the said arabinose.

Advantageously, the process additionally comprises the selection of transformed strains having metabolized arabinose on the basis of their aldose reductase activity less than or equal to 0.002 U/g of protein, even less than or equal to 0.0005 U/g of protein.

In the context of the invention, "yeast strain" is understood to be a population of yeasts rigorously identical from a genetic point of view. This encompasses both strains referred to as laboratory strains and those referred to as industrial strains.

Advantageously, the yeast strain used in said process is chosen from among *Saccharomyces, Schizosaccharomyces, Pichia, Yarrowia, Paffia, Kluyveromyces, Candida, Talaromyces, Brettanomyces, Pachysolen, Hansenula, Kloeckera, Schwanniomyces* and *Debaryomyces* strains, advantageously a *Saccharomyces cerevisiae* strain. These yeasts are known for their inability to metabolize arabinose naturally or at a very low level, not industrially applicable. Moreover, they are advantageously chosen for their anaerobic fermentation capacity, even more advantageously for their anaerobic alcoholic fermentation.

According to a particular embodiment, the process, object of the present application, is carried out on a strain suitable for fermenting xylose, advantageously for fermenting xylose in the presence of an organic acid in non-dissociated form, such as acetic acid. As widely disclosed in prior art, the capacity to metabolize xylose can result in the introduction of a gene coding a xylose isomerase, from *Clostridium phytofermentans* for example, and/or a xylulokinase.

Advantageously, these are the following strains:

the strain registered at the CNCM on Oct. 5, 2011 under number I-4538;

the strain registered at the CNCM on May 16, 2013 under number I-4749;

the strain registered at the CNCM on Dec. 12, 2013 under number I-4829;

the strain registered at the CNCM on Apr. 9, 2015 under number I-4966; more advantageously, the strain registered at the CNCM on Jan. 29, 2015 under number I-4953.

For the purposes of the invention, a yeast strain able to metabolize arabinose is a strain capable of consuming or using arabinose, advantageously L-arabinose, present in its culture medium. Thus and based notably on the culture conditions, a yeast strain can use arabinose for production of its biomass and/or generation of fermentation products. For the purposes of the present application, fermentation of arabinose is understood to be the metabolization of arabinose that takes place in hypoxia and/or anaerobically, that is, under conditions of low availability (typically less than 20%) or entirely absence of oxygen.

Within the meaning of the invention, the term "metabolize" can therefore target as well the ability of the yeast strain to use the arabinose to ensure its growth and its ability to ferment the arabinose in various fermentation products such as of the hydroxy derivatives, including ethanol or isobutanol, and/or carboxylates, including organic acids.

According to a particular embodiment, reference is made to its capacity to convert L-arabinose into L-ribulose and/or L-ribulose-5-phosphate and/or into D-xylulose-5-phosphate and/or into a fermentation product such as ethanol. According to one advantageous embodiment and as seen in FIG. 1, L-arabinose is converted into L-ribulose under the action of an arabinose isomerase (araA; EC: 5.3.1.4). L-ribulose can itself be converted into L-ribulose-5-phosphate under the action of a ribulokinase (araB; EC: 2.7.1.16). L-ribulose-5-phosphate can thus be transformed into D-xylulose-5-phosphate by a ribulose 5 phosphate epimerase (araD; EC: 5.1.3.4). Advantageously, D-xylulose-5-phosphate is carried out by the non-oxydative part of the pentose phosphates pathway and can result in production of ethanol.

In an initial step of the process according to the invention, the gene(s) allowing metabolization of arabinose are introduced into the yeast strain, which is then called the transformed strain.

In the following, the terms "gene" or "sequence" mean a nucleic acid sequence comprising a coding sequence (coding e.g. an enzyme from the pathway of interest) potentially flanked by regulatory sequences, particularly a promoter or a terminator. A coding sequence is optimizable, that is, modifiable to integrate the preferred codons of the host, here a yeast, wherein this sequence is expressed.

According to a particular embodiment, the genes coding the metabolic pathway of arabinose are genetic elements called exogenous or heterologous elements, which can be synthetic or come from other organisms (or sources). Advantageously, they come from microorganisms able to metabolize arabinose, advantageously hemi-ascomycetes such as *Scheffersomyces stipitis*, basidiomycetes and filamentous fungi, or bacteria such as *Erwinia chrysanthemi, Thermoanaerobacterium saccharolyticum, Escherichia coli, Zymomonas mobilis, Bacillus subtilis, Bacillus licheniformis* or *Lactobacillus plantarum*. According to a particular embodiment, these genes come from the bacteria *Bacillus licheniformis* and/or *Escherichia coli*. According to another preferred embodiment, these genes correspond to the gene araA from *B. licheniformis*, to the gene araB of *E. coli* and to the gene araD of *E. coli* as described by Widemann and Boles (2008, Applied and Environmental Microbiology 74, 2043-2050; WO 2008/122354).

The techniques used to introduce DNA into a host (or transformation) are well known to the person skilled in the art and include permeabilization of the membranes by applying an electric field (electroporation), with heat (application of a thermal shock) or chemically, using lithium acetate, for instance.

The genes introduced can be integrated into the genome of the host, notably by homologous recombination or chromosomal integration, advantageously with the use of integrative cassettes, or expressed extrachromosomically using plasmids or vectors. Different types of plasmids, advantageously self-replicating, are well known by the person skilled in the art, differing notably by the origin of replication, the promoter (inducible or constitutive), the marker (resistance to antibiotics or capacity to grow on a selective medium) and the number of copies per cell.

According to one embodiment, the genes coding the arabinose metabolization pathway are chromosomally integrated, advantageously at the HO locus level of the yeast strain, more advantageously at the level of all HO loci of the yeast strain.

Advantageously, the cassette carrying this (these) gene(s) and serving to incorporate or integrate them into the yeast strain lacks a marker, notably antibiotic resistance.

According to another preferred embodiment, the cassette carrying this (these) gene(s) carries no gene coding an arabinose carrier, notably the gene araT.

Proper introduction of the gene(s) can easily be verified by techniques known by the person skilled in the art, using a marker possibly harbored by an expression cassette, for example, or preferably by performing a PCR using primers targeting the gene(s) introduced. Additionally, the same PCR technique can be used to verify integration of the gene(s) at the locus targeted, notably using primers targeting said locus.

In a later step of the process according to the invention, a strain of interest having incorporated and effectively expressing the arabinose metabolization pathway is selected for its ability to metabolize the arabinose present in the culture medium, as the sole carbon source.

In a characteristic manner according to the invention, the selection of the transformants is done directly on a medium containing arabinose as the sole carbon source. In other words, the capacity of a yeast strain to metabolize arabinose is tested by culturing the said strain on a medium containing arabinose as the sole carbon source. This excludes any previous induction, particularly a previous culture in the presence of galactose or addition of galactose to the medium, or a preselection of transformants on a medium containing another carbon source such as glucose.

In the scope of the invention, a culture or growth medium is a medium containing the ingredients required for multiplication of the strains present. It advantageously concerns a complete medium suited to the growth of yeast that can contain conventional ingredients such as salts, buffers, yeast extract or any other source of nitrogen the yeast can metabolize, vitamins, etc. In the context of the invention, "synthetic medium" is understood to be a medium whose chemical composition is known.

In an adequate manner, the culture conditions used are conditions favorable to the growth of yeast, particularly:
  a culture medium with acid pH, advantageously between 4 and 6, even 4.5 and 5.5, more advantageously equal to 5 or 5.4;
  a temperature between 28 and 37° C., even between 30 and 35° C., advantageously equal to 32° C.;
  a growth time ranging from 24 hours to several days, 72 hours for example.

Advantageously, this growth takes place in a solid medium, making it possible to isolate the strains that are actually able to metabolize the arabinose. According to another advantageous embodiment, the selection of strains of interest is made using cultures in a Petri dish. In a known manner, the solid media contain agar, advantageously at a concentration of 15 to 20 g/L.

According to an first embodiment, a yeast strain able to metabolize arabinose is selected by aerobically growing this strain in a growth medium containing arabinose as the sole carbon source.

One medium suitable for this aerobic growth is the synthetic medium YNB Difco®, the exact composition of which is given in the examples, containing arabinose as the sole carbon source, advantageously at a concentration of 10 g/L, such as the medium referred to hereafter as YNB-Ara.

Alternatively, a yeast strain able to metabolize arabinose can be selected by growth under anaerobic conditions or in hypoxia in a growth medium containing arabinose as the sole carbon source.

One medium suitable for this anaerobic growth or growth in hypoxia is the synthetic medium YF, the exact composition of which is given in the examples, containing arabinose as the sole carbon source, advantageously at a concentration of 70 g/L, as the medium referred to hereafter as YF-ara.

Advantageously, this medium is suitable for growth in a solid medium, adding agar for example, thus allowing direct isolation of the strains of interest.

According to an alternative embodiment, the yeast strains into which the arabinose metabolization pathway was introduced are isolated by culturing in a solid medium, advantageously in a selective medium such as the YNB-Ara medium described above, then selected in a liquid medium under anaerobic conditions or in hypoxia, into a suitable medium such as the YF-ara medium described above. Said liquid cultures can be carried out in microplates like Deep Weel or in vials, under agitation, for example 100 rpm, or without agitation and under conditions of reduced oxygen supply (under limited $O_2$ or anaerobiosis).

Under these conditions, the ability of the yeast strains to metabolize arabinose can be evaluated by:
  their growth, notably by monitoring the optical density (OD) of the culture medium, advantageously measured at 600 nm; and/or
  the fermentation of arabinose, notably by monitoring the concentration of arabinose present in the culture medium, by HPLC for example, or by evaluating the loss of mass correlated directly with the production of $CO_2$, which is stoichiometric with that of ethanol.

Note that to the Applicant's knowledge, this is the first time the possibility of selecting yeast strains able to metabolize arabinose directly by growing them on a medium containing arabinose as the sole carbon source has been reported. To the contrary, it was deemed that the person skilled in the art would have been dissuaded from using such an approach given that information in Wisselink et al. (2007; Appl Environ Microbiol 73, 4881-4891; WO 2008/041840) who reported that such a direct selection did not work.

According to another advantageous embodiment, the yeast strains obtained can also be tested at the same time or subsequently under the following conditions:
  on a growth medium containing glucose as the sole carbon source, for example on a YF medium as described above, but containing 150 g/L of glucose, and under the culture conditions given above. This step makes it possible to verify the validity of the selected strains, notably their ability to ferment glucose. Note that one or more passages on glucose medium can be made before growing the selected strains onto a medium containing arabinose as the sole carbon source (described above) and verifying that the phenotype [ara+] is stable and preserved;
  on a growth medium containing xylose as the sole carbon source, for example on a YF medium as described above, but containing 70 g/L of xylose (YF-xylose medium in the examples), and under the culture conditions given above. This step makes it possible to verify that the strains selected retain their capacity to ferment xylose and show an interest when the yeast strain onto which the invention process is used is capable of fermenting xylose.

Additionally and in the framework of the invention, it was shown that an important criterion in the selection of strains of interest for metabolization of arabinose was their polyol production level.

In a known manner, polyols such as xylitol possess an inhibiting effect on xylose isomerase (xylA) activity (Kovalevsky et al., 2012, Acta Crystallogr. D Biol. Crystallogr. 68, 1201-1206). In the framework of the present invention, it has been evidenced that polyols could also inhibit arabinose isomerase activity (araA; FIG. 1) and thereby decrease arabinose metabolization of a strain selected by the process according to the invention.

Arabitol is likely to be generated from arabinose under the action of aldose reductase(s), in the same way that xylitol is generated from xylose. It should be noted that in a known manner, the GRE3 gene codes the main aldose reductase in S. cerevisiae but that, even when it is deleted or deactivated, an aldose reductase activity can persist. Moreover, the presence of a xylitol dehydrogenase activity in yeast strains has the potential to eliminate xylitol.

Thus, and according to this assumption, a strain selected for particular interest shows:
  a strong polyol dehydrogenase activity, advantageously greater than or equal to 0.001 U/g of protein, or even more advantageously greater than or equal to 0.002 U/g of protein; and/or
  a low aldose reductase activity.

In practice and in the framework of the invention, it has been highlighted that a strain of interest could be selected based on its low, even null, aldose reductase activity. Advantageously, this activity is lower than 0.005 U/g of protein, even 0.004, 0.003, or even 0.002 U/g of protein. More preferably, it is less than or equal to 0.0015 U/g of protein, even less than or equal to 0.001 U/g of protein, more advantageously less than or equal to 0.0005 U/g of protein.

A detailed protocol for measuring aldose reductase activity is described in the "Examples".

Further and advantageously, the yeast strain used in the process according to the invention shows one or more deleted or inactive GRE3 genes.

According to another preferred embodiment, a yeast strain used in the present invention shows at least one supernumerary copy of the HAA1 gene coding the transcriptional regulator Haa1p. In a known manner, the former is able to give the yeast strains, specifically S. cerevisiae, the ability to resist to acetic acid, thus improving growth in a medium containing fermentation inhibitors of the organic acid type, such as acetic acid. Additionally, the Applicant has shown that overexpression of this gene would make it resistant to other phenolic compound inhibitors, in particular vanillin.

Advantageously, expression of the supernumerary gene coding Haa1p is placed under control of a heterolog promoter, the pPGK1 promoter for example. This supernumerary copy of gene HAA1 may code the native protein or a mutated form of it, for example the constitutively active version $HAA1_{S135F}$, described by Swinnen et al. (2017, Microbial Cell Factories 16: 7).

According to a preferred embodiment, the additional copy of the HAA1 gene is integrated at the chromosome level, even more advantageously by inserting at the GRE3 gene level. From that, there are two advantageous results in the frame of the invention, which are:

inactivation of the GRE3 gene coding an aldose reductase;

the overexpression of the HAA1 gene makes the yeast strains more resistant to acetic acid but also to vanillin.

The second step in the process according to the invention corresponding to the selection step of the yeast strains of interest, can be used to evaluate either of the 2 aforementioned criteria, advantageously both. According to a particular embodiment, the ability to metabolize the arabinose present in the culture medium is evaluated first, then the strains selected are tested for their aldose reductase activity.

The interest in the strains thus selected, notably their ability to ferment arabinose but also glucose and possibly xylose, can be confirmed by evaluating their performance on synthetic media containing the different sugars in mixture, that is, arabinose and glucose, even arabinose, glucose and xylose in the case of strains of origin able to ferment xylose. In order to mimic actual fermentation conditions, these media also contain acetic acid, advantageously at a concentration from 1 to 10 g/L, known to inhibit fermentation of glucose and xylose.

Examples of such media are YPF or YFCF, the composition of which is given below:

YFCF Medium:
  10 g/L of yeast extract;
  10 g/L of bacto-peptone;
  63 g/L of glucose;
  28 g/L dexylose;
  28 g/L of arabinose;
  4 g/L of acetic acid (quantity added to the culture medium at pH 5).

YFP Medium:
  10 g/L of yeast extract;
  10 g/L of bacto-peptone;
  63 g/L of glucose;
  52 g/L de xylose;
  6.1 g/L pf arabinose;
  4 g/L of acetic acid (quantity added to the culture medium at pH 5).

Standard culture conditions favorable for production of ethanol in the yeast are:
  an acidic and stable pH, advantageously between 4 and 6, for example equal to 5;
  a temperature between 28 and 37° C., even between 30 and 35° C., advantageously equal to 30° C.;
  low agitation, 100 rpm for example;
  reduced conditions of oxygen supply (under limited $O_2$). In practice, the culture can be made in a stoppered flask using a cap that reduces the supply of $O_2$ in the medium while allowing evacuation of the $CO_2$ produced;
  seeding with an inoculum of 0.25 g/kg eq MS of the strain propagated under saturation on YPG for 24 hours;
  a growth time of at least 24 hours, 72 hours for example.

In the framework of the invention, the strains selected via this procedure reveal:
  the ability to use arabinose as the sole carbon source to ensure production of their biomass;
  the capacity to ferment arabinose;
  the capacity to ferment glucose, and possibly xylose, even in the presence of an organic acid in non-dissociated form, acetic acid in particular.

It was observed after 72 hours of fermentation under the conditions described above:
  consumption of 95%, even all, of the glucose and xylose present in the culture medium, converted into either biomass, or ethanol and $CO_2$;
  consumption of more than 50%, even 60%, 70%, or even 80% of the arabinose present in the culture medium.

Thus and according to an additional aspect, the present invention relates to a yeast strain obtainable using the process described, capable of fermenting at least 50%, even 60%, 70% or even 80% of the arabinose after 72 hours of fermentation in a medium comprising glucose (advantageously at a concentration of 1 to 100 g/L, e.g. 63 g/L), xylose (advantageously at a concentration of 1 to 100 g/L, e.g. 28 or 52 g/L), arabinose (advantageously at a concentration of 1 to 100 g/L, e.g. 6.1 or 28 g/L) and acetic acid (advantageously at a concentration of 1 to 10 g/L, e.g. 4 g/L). Preferably, such a yeast strain is able to ferment at the same time at least 90%, even 95%, of the glucose and xylose also present.

Such a strain also shows advantageously at least one of the following characteristics, even all the characteristics:
  at least one copy of a gene araA, preferably from *B. licheniforma*, advantageously integrated at the chromosome level, more advantageously at the level of at least one HO locus;
  at least one copy of the gene araB, preferably from *E. coli*, advantageously integrated at the chromosomal level, more advantageously at the level of at least one HO locus;
  at least one copy of the gene araD, preferably from *E. coli*, advantageously integrated at the chromosomal level, more advantageously at the level of at least one HO locus;
  at least one copy of an exogenous gene coding a xylose isomerase, advantageously from *Clostridium phytofermentans*;
  at least one supernumerary copy of the gene GAL2, coding a transporter of hexoses also capable of ensuring the capture of xylose. According to another embodiment, said strain comprises at least two supernumerary copies of the GAL2 gene. This can be placed under the control of a strong and constitutive promoter of the pADH1-type;
  suppression of the aldose reductase activity coded by GRE3, advantageously by insertion of the HAA1 gene at the level of locus GRE3;
  overproduction of xylulokinase (XKS1), in particular by modification of the promoter or introduction of supernumerary copies;
  the expression or overproduction of the pentose phosphate pathway (RPE1, RKL1, TKL1, TAL1, etc.);
  absence of xylose reductase (XR) activity.

According to a particular embodiment, such a strain is not muted at the following genes level: SSY1, YJR154w, CEP3, GAL80 and/or PMR1. According to another particular embodiment, the strain does not carry the following mutations: G1363T in the SSY1 gene, A512T in the YJR15w gene, A1186G in the CEP3 gene, A436C in the GAL80 gene, A113G in the PMR1 gene.

A strain of particular interest, obtained by using the process claimed, is the strain deposited under the Budapest treaty at the CNCM (Collection Nationale de Cultures de Microorganismes, Institut Pasteur, 25 rue du Docteur Roux, 75724 Paris Cedex 15) on May 19, 2016 under number I-5085.

According to another aspect, the invention concerns a process for obtaining and/or selecting yeast strains with an improved ability to ferment arabinose, xylose and glucose in the presence of organic acid fermentation inhibitors, particularly acetic acid, characterized notably by an increase in the production of ethanol and by a greater consumption of the arabinose present in the medium.

The invention also concerns a process for obtaining and/or selecting a yeast strain with an improved capacity to ferment glucose, xylose and arabinose, advantageously in the presence of an organic acid in non-dissociated form such as acetic acid wherein a yeast strain showing such a capacity is cultivated successively under the following conditions:

an anaerobic culture in a first medium containing, as the sole carbon sources, arabinose and xylose in limited amounts for production of the biomass; then two successive anaerobic cultures, one in a medium containing glucose as the sole carbon source and the other in a medium containing xylose as the sole carbon source in the presence of organic acid in non-dissociated form, advantageously acetic acid;

optionally, an aerobic culture in a minimum medium containing, as the sole carbon source, a source of strict respiratory carbon, advantageously glycerol.

Such a process is therefore to achieve a directed evolution of the yeast strains used. Without wanting to be held to any one theory, the selection pressure exerted by the consecutive cultures in the growth media defined below allows the strain to acquire the phenotypic traits necessary for increasing its ability to ferment arabinose and retain its ability to ferment xylose and glucose in the presence of organic acid in non-dissociated form, acetic acid in particular.

Thus, the process according to the invention allows to select, from an isolated strain or a mixture of strains, one strain having a selective advantage in terms of growth on a medium containing these three sugars and said organic acid in non-dissociated form.

Said process, also subject of the present application, can be used on an isolated strain, particularly on the strain registered at the CNCM (Collection Nationale de Cultures de Microorganismes, Institut Pasteur, 25 rue du Docteur Roux, 75724 Paris Cedex 15) on May 19, 2016, under number I-5085.

According to said process, the yeast strain or mixture of strains is cultivated consecutively in at least three growth media. As previously stated, the expressions "growth medium" and "culture medium" are used interchangeably to designate a medium comprising the ingredients necessary for the multiplication of the yeasts that are present.

The first growth medium, advantageously liquid, is characterized in that it contains the pentoses arabinose and xylose as the sole carbon sources.

It should be noted that it is traditionally agreed that, when a population of yeasts has two sugars, it generally uses only one to make the biomass. Once this first sugar is consumed, the second can be used. Thus, there was a real risk in the stability of the fermentation phenotype of the two pentoses—xylose and arabinose.

In a characteristic manner according to the invention, the first medium contains a concentration of pentoses that makes it possible to cover 100%, advantageously 50% each, of the yeast strain's carbon needs. According to another embodiment, arabinose and xylone are present in equivalent concentrations, for example, at a rate 30 of 5 g/L for the arabinose and 4 g/L for the xylose.

According to another preferred characteristic, it is a synthetic medium the exact composition of which is controlled, advantageously a medium whose chemical compound is entirely determined. Such a medium is named for example "GO xylose arabinose", the composition of which is given in the examples. Note that in such a medium, it is not the nitrogen source that limits biomass production (10 g/L of $(NH_4)_2PO_4$) but the amount of carbon sources, in the case at hand xylose (4 g/L) and arabinose (5 g/L). Thus, such a medium favors the growth and multiplication of yeast strains that use both sugars.

The following step is designed to anticipate a possible risk of loss of tolerance to inhibitors of the selected strains, particularly acetic acid in non-dissociated form.

Thus, in this step two successive anaerobic cultures are implemented:

one in a growth medium containing glucose as the sole carbon source; and the other in a growth medium containing xylose as the sole carbon source.

The order of passage on the two culture media can optionally be inverse (xylose medium, then glucose medium).

Advantageously, the concentration of glucose or xylose in the growth medium is that commonly implemented when it is used as the only carbon source, specifically comprised between 5 and 200 g/L in the case of a liquid medium (5 and 200 g/kg in the case of a solid medium), for example equal to 150 g/L for glucose and 70 g/L for xylose.

Advantageously, said medium also includes the organic acid capable of inhibiting fermentation of both sugars. It advantageously involves acetic acid or formic acid, still more advantageously acetic acid.

It should be noted that it is known that only the non-dissociated or non-ionized form of such acids have inhibition ability. In the context of the invention, "non-ionized or non-dissociated form" of a carboxylic acid is understood as the protonated form thereof. In practice, the form of such organic acids depends on the pH of the medium in which they are incorporated. At a pH greater than the pKa of the acid, the acid will be mostly found in dissociated form or $COO^-$ ions. In contrast and at a lower pH, the majority form is the non-dissociated or non-ionized form (COOH). In the rest of the description, reference is made to acetic acid added to the medium, encompassing dissociated and non-dissociated forms according to the pH of said medium.

Advantageously, the concentration of the organic acid, advantageously as acetic acid, in non-dissociated form in the growth medium is comprised between 0.5 and 5 g/L in liquid medium (equivalent to 0.5 and 5 g/kg in solid medium), advantageously between 1.3 and 2.6 g/L. In practice and as an example, this final range corresponds to a concentration of acetic acid added to a growth medium at pH 5 comprised between 3 and 6 g/L, e.g. 4 or 5 g/L.

In addition to these two ingredients, said growth medium is advantageously a complete synthetic medium adapted to the growth of yeasts anaerobically or in hypoxia, e.g. the YF medium wherein the exact composition is given in the examples.

The media suitable for the implementation of the second step of the process according to the invention are for example the media called YF-glucose acid and YF-xylose acid, the composition of which is detailed in the examples.

Beyond the specific composition of these growth media, the culture of the yeast strain or mixture of strains in these first and second steps of the process according to the invention is advantageously made under standard conditions favorable to the growth of yeasts, in particular *Saccharomyces* type, under anaerobiosis or hypoxia, and their fermentation activity, specifically:

an acid pH advantageously comprised between 4 and 6, even 4.5 and 5.5, even more advantageously equal to 5 or 5.4;

a temperature between 28 and 37° C., even between 30 and 35° C., advantageously equal to 32° C.;

under gentle stirring, for example equal to 100 rpm;

under reduced conditions of oxygen supply (under limited 02). In practice, the culture can be made in a flask stoppered using a cap reducing the supply of 02 in the medium while allowing evacuation of the $CO_2$ produced.

Generally, the culture is stopped when the source of hydrolyzable glucidic carbon has been completely consumed. In practice, and advantageously, the culture is left for at least 24 hours, even several days, advantageously for up to seven days.

According to a specific embodiment, the method according to the invention further comprises the passage of the yeast into a fourth growth medium, advantageously liquid, intended to select the cells capable of respiration, specifically having functional mitochondria. In practice, this step, which can be implemented with each cycle or at least once in the method, serves to overcome the appearance of "petites" whose respiratory-deficient phenotype can be disadvantageous in the context of industrial yeast production methods.

Advantageously, this fourth medium is a poor or minimum medium containing as the only carbon source a carbon which can only be used by cells which retained functional mitochondria. In this case, one is speaking of a source of strict respiratory carbon, meaning a carbon source systematically involving mitochondrial oxidation and not producing ethanol. It can advantageously be glycerol or possibly ethanol. In other words, such a medium is free of fermentable sugar.

Advantageously, the glycerol concentration of the growth medium is that commonly used when it is used as the only carbon source, specifically comprised between 5 and 50 g/L, advantageously comprised between 10 and 50 g/L, for example equal to 10 g/L so as to obtain sufficient biomass for inoculating the first culture medium of the following cycle.

By definition, a minimum medium contains, further to a carbon source, a nitrogen source, a potassium source, a phosphorous source, a sulfur source, a magnesium source, a calcium source, an iron source, a source of trace elements and of water.

A medium which can be used for preparation of this culture medium may include:
  a base, such as DIFCO® yeast nitrogen base, advantageously at a concentration of 3.4 g/L;
  and optionally ammonium sulfate, advantageously at a concentration of 5 g/L.

Beyond the specific composition of this growth medium, the culture of the yeast strain or mixture of strains is advantageously made under standard conditions favorable to the growth of yeasts in aerobiosis, specifically:
  an acid pH advantageously comprised between 4 and 6, even 4.5 and 5.5, for example equal to 5;
  a temperature between 28 and 37° C., even between 30 and 35° C., advantageously equal to 32° C.;
  under medium agitation, for example equal to 150 rpm;
  in aerobiosis. In practice, the culture can be made in a baffled flask stoppered by a porous cap which allows the supply of 02 in the medium.

There again, the culture is stopped when the carbon source, advantageously glycerol, has been completely consumed. In practice and advantageously, the culture is done over several hours, advantageously 48 hours.

Said succession of culture in these three, even four, media and under the conditions described, constitutes one cycle.

In practice, a selection cycle according to the invention can be as follows:
  A first anaerobic or hypoxia culture in the presence of xylose and arabinose;
  A second anaerobic or hypoxia culture in the presence of glucose and acetic acid;
  A third anaerobic or hypoxia culture in the presence of xylose and acetic acid;
  Possibly a fourth anaerobic culture in the presence of glycerol;
or
  A first anaerobic or hypoxia culture in the presence of xylose and arabinose;
  A second anaerobic or hypoxia culture in the presence of xylose and acetic acid;
  A third anaerobic or hypoxia culture in the presence of glucose and acetic acid;
  Possibly a fourth anaerobic culture in the presence of glycerol.

According to the invention, these different cultures are made according to the "Single Batch Repeat" method, e.g., without renewal of the culture media present.

According to a particular embodiment, such cycle is repeated at least twice ("Multiple Batch Repeat"), e.g. 2 times.

This process enabled selection of yeast strains that, during fermentation on a medium approaching the natural media containing arabinose, glucose, xylose and acetic acid, present an improved ethanol production (a higher alcohol strength) and a better consumption of arabinose present in the medium.

According to another aspect, the present invention relates to a yeast strain obtained using the method described above. It was thereby possible to isolate yeast strains that, at the end of this selection process, have a capacity for the consumption of arabimose present in the medium increased by at least 10%, even 20%, 30%, 40%, 50%, 60%, 70%, or even more 80%. These performances are advantageously evaluated under fermentation conditions hereabove described in relation to the medium YFCF and after 160 hours.

In fact, under these conditions, consumption of over 90%, even 95% or even 97.5% of arabinose present in the culture medium was observed.

Thus and according to an additional aspect, the present invention relates to a yeast strain obtainable using the process described, which is capable of fermenting at least 90%, even 95% or even 97.5% of arabinose after 160 hours of fermentation in a medium comprising glucose (advantageously in an amount of 1 to 100 g/L, e.g. 63 g/L), xylose (advantageously in an amount of 1 to 100 g/L, e.g. 28 g/L), arabinose (advantageously in an amount of 1 to 100 g/L, e.g. 28 g/L) and acetic acid (advantageously in an amount of 1 to 10 g/L, e.g. 4 g/L). Preferably, such a yeast strain is capable of fermenting at the same time at least 90%, even 95%, or even 100% of the glucose and xylose present.

Such a strain also shows advantageously at least one of the following characteristics, even all the characteristics:
  at least one copy of an araA gene, preferably from *B. licheniforma*, advantageously integrated at the chromosomal level, more advantageously at the level of all HO loci;
  at least one copy of an araB gene, preferably from *E. coli*, advantageously integrated at the chromosomal level, more advantageously at the level of all HO loci;
  at least one copy of the araD gene, preferably from *E. coli*, advantageously integrated at the chromosomal level, more advantageously at the level of all HO loci;

at least one copy of an exogenous gene coding a xylose isomerase, advantageously from *Clostridium phytofermentans*;

at least one supernumerary copy of the GAL2 gene, coding a transporter of hexoses also capable of ensuring capture of xylose. According to another embodiment, said strain includes at least two supernumerary copies of the GAL2 gene. This can be placed under the control of a strong and constitutive promoter of the pADH1-type;

suppression of the aldose reductase activity coded by GRE3, advantageously by insertion of the HAA1 gene into the GRE3 locus;

overproduction of xylulokinase (XKS1), notably by modifying the promoter or introducing supernumerary copies;

the expression or overproduction of the pentose phosphate pathway (RPE1, RKI1, TKL1, TAL1, etc.);

absence of xylose reductase (XR) activity.

According to another advantageous embodiment, such a strain presents at least one of the following characteristics, advantageously both:

Strong polyol dehydrogenase activity, advantageously greater than or equal to 0.001 U/g of protein, still more advantageously greater than or equal to 0.002 U/g of protein;

Aldose reductase activity less than 0.005 U/g of protein, even 0.004, 0.003, or even 0.002 U/g of protein, preferably less than or equal to 0.0015 U/g of protein, even less than or equal to 0.001 U/g of protein, most preferably less than or equal to 0.0005 U/g of protein.

According to a particular embodiment, such a strain is not mutated at the level of the following genes: SSY1, YJR154w, CEP3, GAL80 and/or PMR1. According to another particular embodiment, the strain does not carry the following mutations: G1363T in the SSY1 gene, A512T in the YJR154w gene, A1186G in the CEP3 gene, A436C in the GAL80 gene, A113G in the PMR1 gene.

A strain of particular interest is the strain deposited under the Budapest treaty at the CNCM (Collection Nationale de Cultures de Microorganismes, Institut Pasteur, 25 rue du Doctor Roux, 75724 Paris Cedex 15) on May 19, 2016, under number I-5086.

According to a particular embodiment, such a strain has at least one supernumerary copy of the HAA1 gene, advantageously inserted at the GRE3 gene level.

According to another aspect, the present invention also targets a yeast obtained by culture of the strains as defined above.

In the context of the invention, "yeast" is understood to be a commercial product obtained by implementing a process for the production of a yeast strain. Thus, yeasts having different properties can be obtained from a single strain, where these differences are connected with the production method implemented.

According to another aspect, the invention concerns the use of strains or yeasts as defined above for the fermentation of a material, advantageously containing arabinose and/or xylose and/or glucose, and/or for the production of ethanol.

According to a specific embodiment, the material is a lignocellulose material. Such material typically contains:

pentoses, in particular D-xylose and L-arabinose;
hexoses, in particular D-mannose, D-galactose, L-rhamnose and D-glucose;
uronic acids.

According to a specific aspect, the invention concerns a production method of fermentation products or ethanol comprising the following steps:

Incubation of a material or medium containing arabinose and/or xylose and/or glucose, advantageously arabinose, xylose and acetic acid, with a strain or a yeast as defined above;

Fermentation under anaerobic or semi-anaerobic (hypoxia) conditions;

Recovery of the one or more fermentation products, or ethanol.

According to a particular embodiment, the material or medium is hemicellulose, or "corn fibers".

The present invention is going to be illustrated more ahead using the following examples, supported by the attached figures. However, they have no limiting scope.

LEGENDS FOR THE FIGURES

Figure 3:
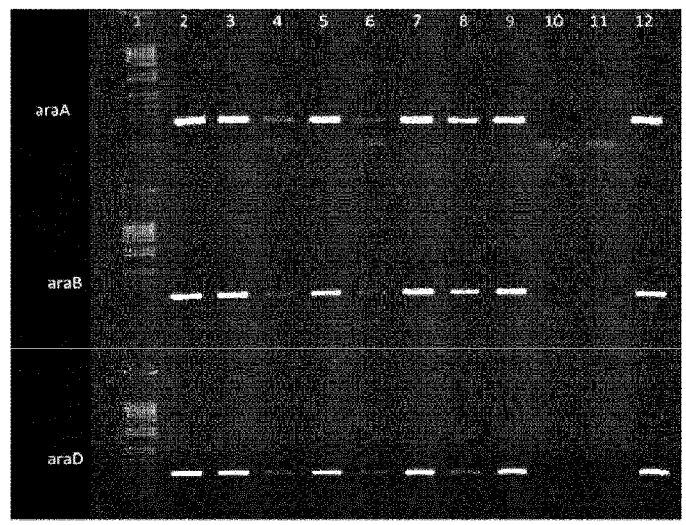

FIG. 3 shows the PCR products obtained by using the oligonucleotides in Table 1 below. Track 1 corresponds to a size marker (1 kb DNA ladder), tracks 2 to 9 correspond to PCR products obtained by using the DNA genomic matrix of the 8 transformers tested, track 10 is obtained with the non-transformed strain. Track 11 is the negative control of the technique (water) and track 12 is the positive control with plasmid pL1285-055 as a matrix.

Figure 4:
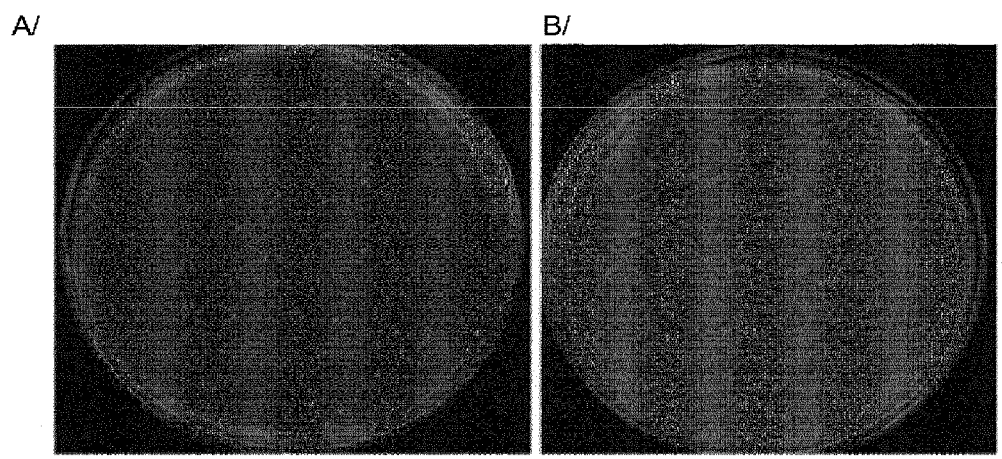

FIG. 4 illustrates the growth of the colonies on a YPG medium+blasticidin 50 mg/L (A) and on a YNB-Ara medium containing 10 g/L of arabinose (B).

Figure 5:
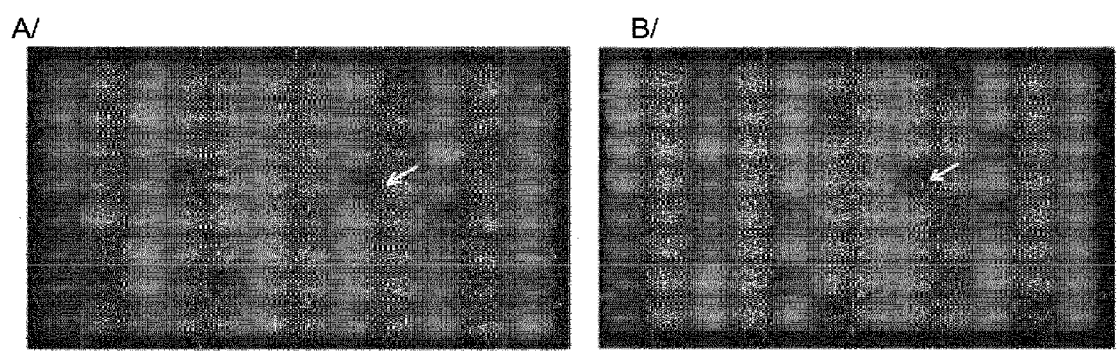

FIG. 5 illustrates the growth of the clones selected, on a medium containing arabinose (A) or xylose (B) as the sole carbon source.

Figure 6:
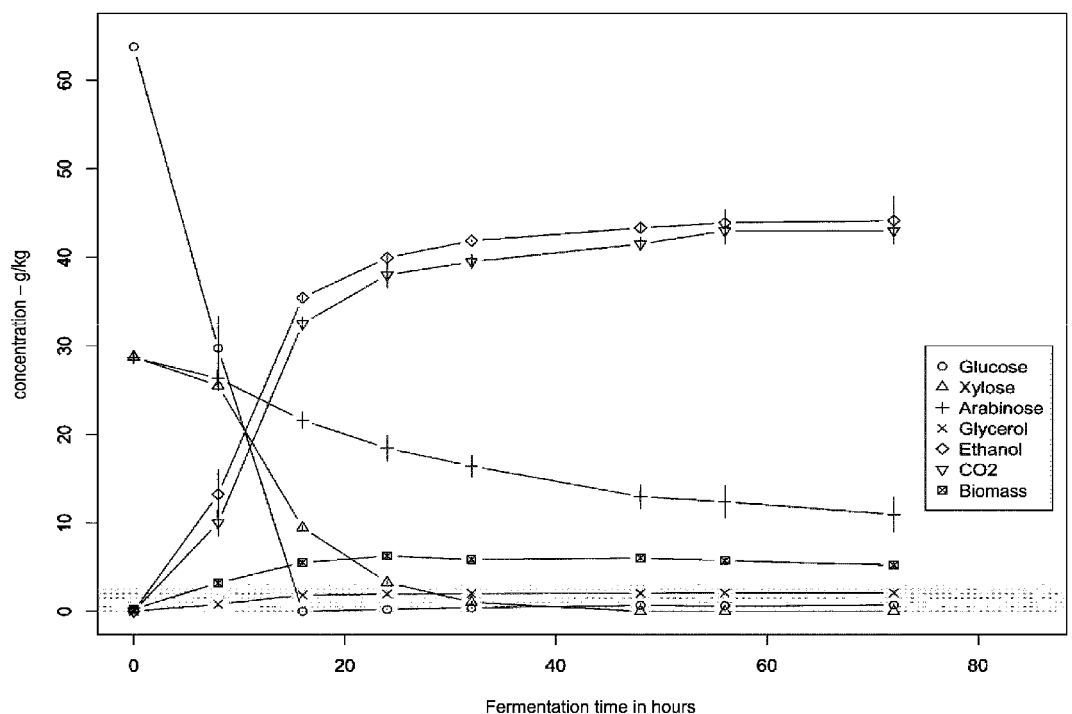
Figure 6:
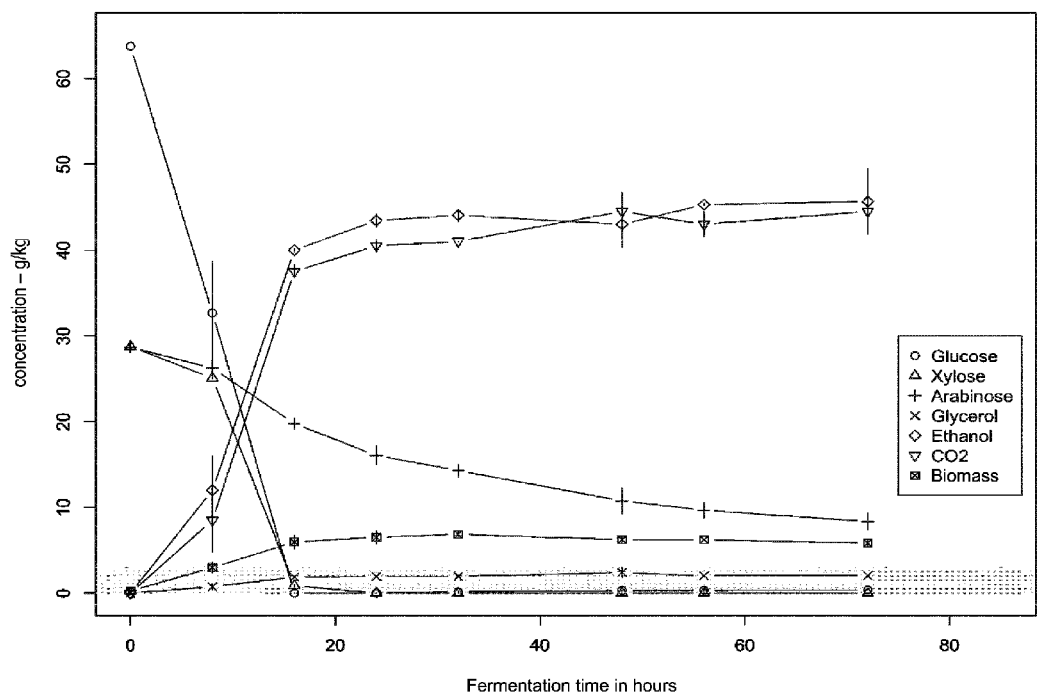

FIG. 6 represents the evolution of the concentration (expressed in g/kg) of the various constituents based on fermentation time, on a YFCF medium (63 g/kg of glucose, 28 g/kg of xylose, 28 g/kg of arabinose and 4 g/kg of acetic acid pH=5), by clones 13 (A) and 126 (B) selected for their ability to ferment arabinose. The values represent the average values from 3 biologically independent experiments.

Figure 7:
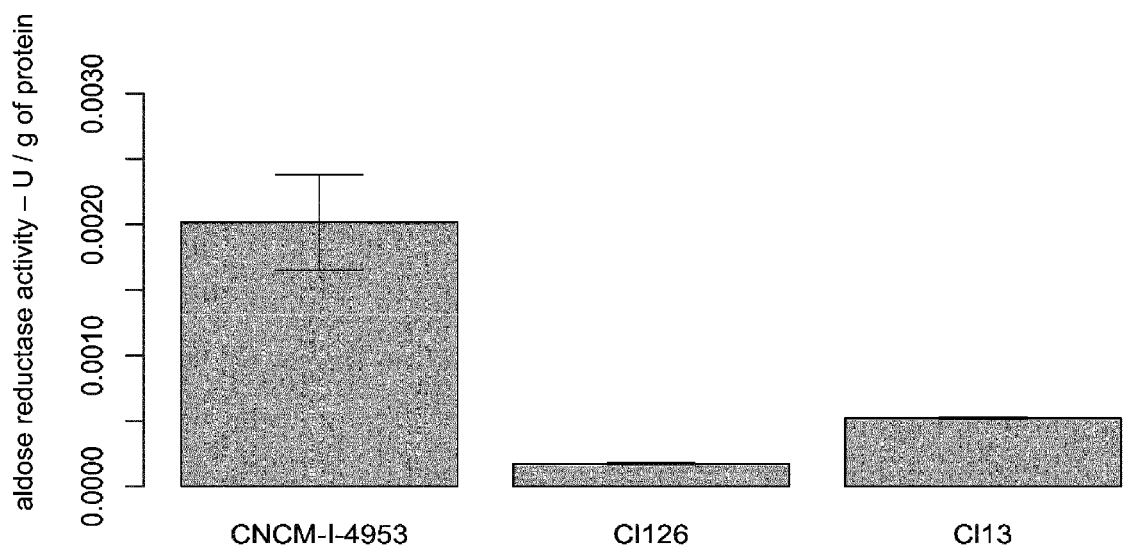

FIG. 7 represents the aldose reductase activity measured in different gene pools tested (1-4953; clone 13; clone 126). The values represent the average values from 2 biologically independent experiments.

Figure 8:
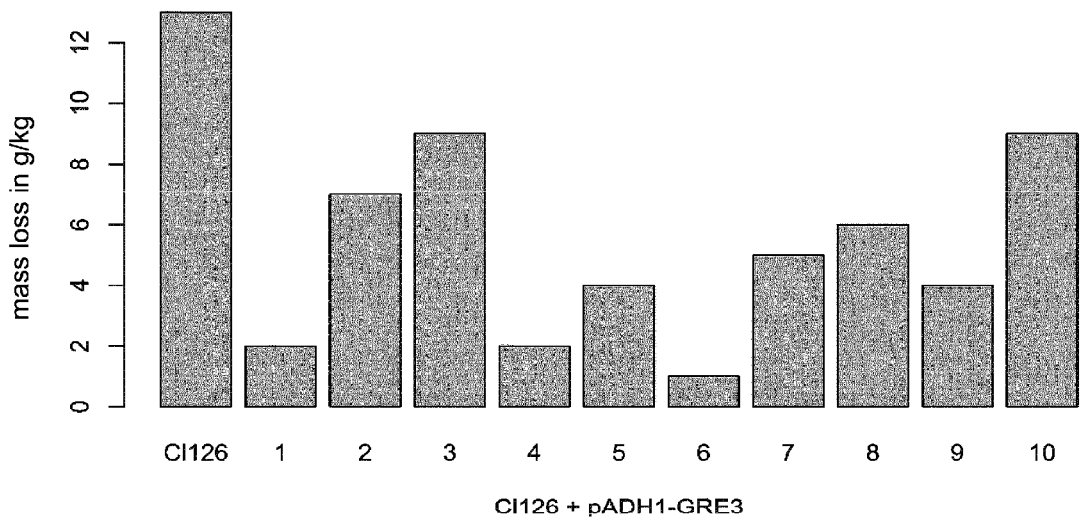

FIG. 8 represents the loss of mass observed after 48 hours fermentation in clone 126 and transformers (transformed with pADH1-GRE3).

Figure 9:
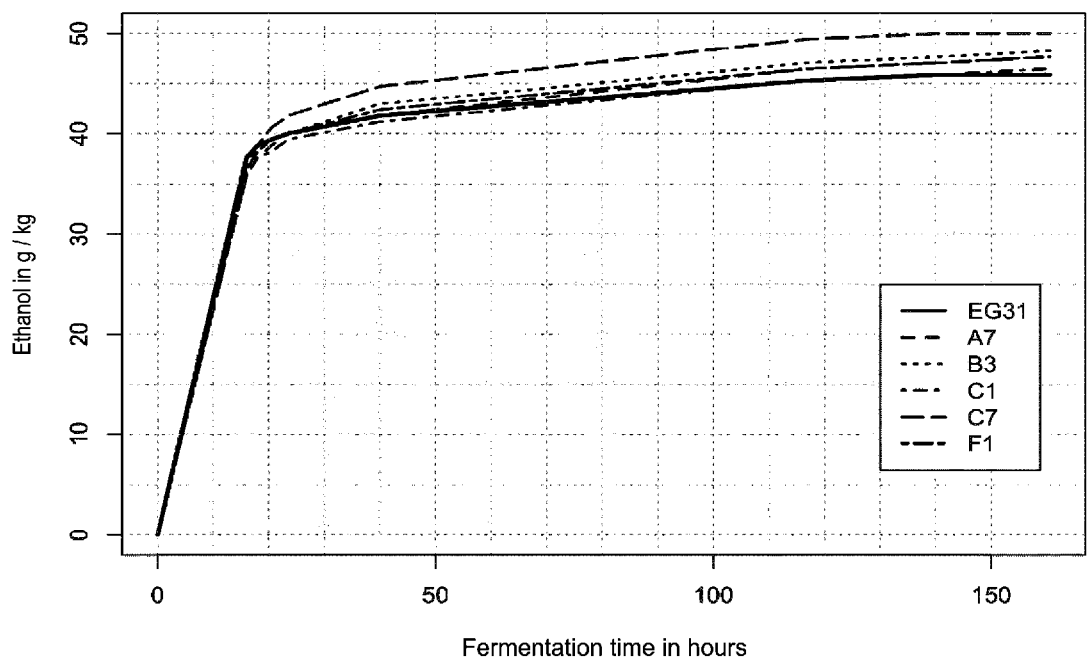
Figure 9:
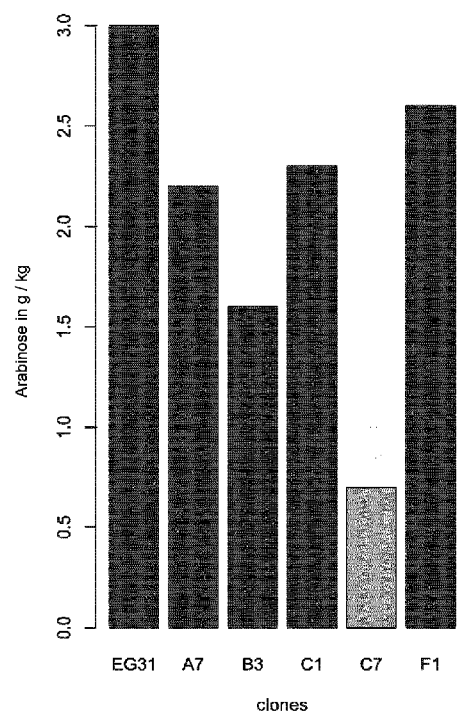

FIG. 9 shows (A) the change in ethanol concentration (g/kg) as a function of the fermentation time on a YFCF medium of different clones selected after a directed evolution made from strain EG31; (B) the concentration of arabinose (g/kg) after 160 hours of fermentation on YFCF medium of these same clones and strain EG31.

EXAMPLES

Figure 1:
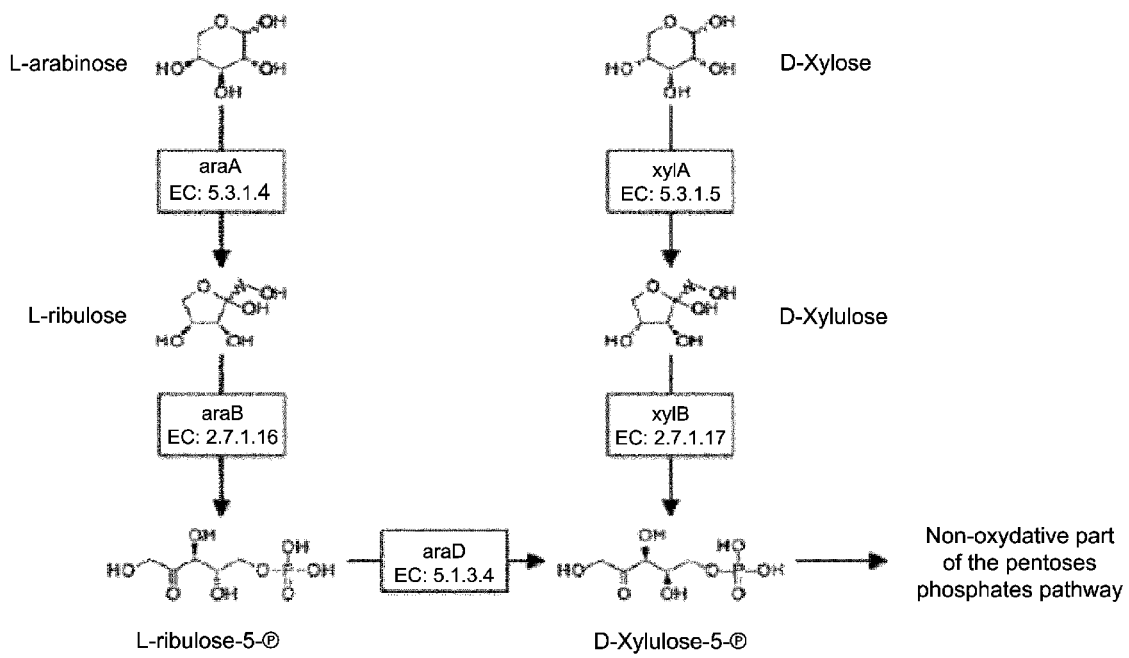
FIG. 1 shows the metabolic pathways for converting L-arabinose and D-xylose into D-xylulose-5-phosphate.

I/ Obtaining a Strain of *Saccharomyces cerevisiae* Able to Ferment Arabinose:

1. Transformation by the Arabinose Pathway:

The pathway to ferment arabinose is shown in FIG. 1.

Figure 2:
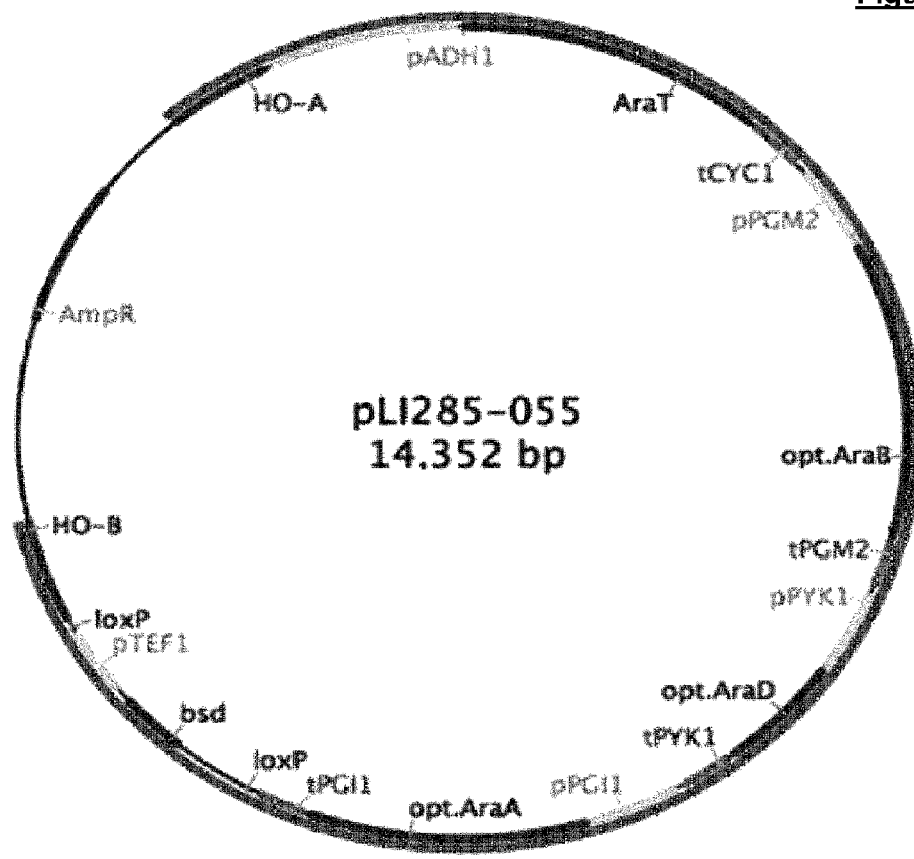
FIG. 2 shows plasmid pL1285-055 permitting integration of genes araA/araB/araD at the level of the HO locus of *Saccharomyces cerevisiae*.

Strain noted I-4953, deposited under the Budapest treaty at the CNCM (Collection Nationale de Cultures de Microorganismes, Institut Pasteur, 25 rue du Docteur Roux, 75724 Paris Cedex 15) under number CNCM I-4953 on Jan. 29, 2015, was transformed with plasmid pL1285-055 (FIG. 2), a derivative of plasmid pHD22 bearing an expression cassette of the arabinose pathway permitting integration of 5 genes araA of *Bacillus lichenformis* and araB/araD of *Escherichia coli* at the level of the HO locus of this strain of *S. cerevisiae*.

This strain is also known for its ability to metabolize xylose due to the presence of at least one copy of an exogenous gene coding xylose isomerase from *Clostridium phytofermentans*.

Furthermore, this strain overexpresses genes coding enzymes from the non-oxidative part of the pentose phosphates pathway, notably genes TAL1 and TKL1.

2. Validation of the Chromosomal Integration of the Arabinose Pathway:

Proper integration of the various genes that code the enzymes forming the metabolization pathway of arabinose, particularly genes araA, B and D, was verified by PCR using genomic DNA of the transformants as the matrix and oligonucleotides amplifying a fragment of each of the corresponding 3 ORF. Said oligonucleotides and their sequence are shown in Table 1 below:

| Name | Sequence | Expected size |
|---|---|---|
| araA-v-f-1 (SEQ ID NO: 1) | ATGATTCAAGCTAAGACCC | 350 pb |
| araA-v-r-1 (SEQ ID NO: 2) | ATGTCAATCTTGTCCCATGG | |
| araB-v-f-1 (SEQ ID NO: 3) | ATGGCTATTGCTATTGGTTT | 357 pb |
| araB-v-r-2 (SEQ ID NO: 4) | CCACAAAACGAACATAGCGT | |
| araD-v-f-1 (SEQ ID NO: 5) | ATGTTGGAAGACTTGAAGAG | 363 pb |
| araD-v-r-1 (SEQ ID NO: 6) | TAGAAGTAGTCAGCGTGGGT | |

The PCR products obtained were analyzed on an agarose gel at 0.8% after an hour of migration at 50 Volts in TAE 0.5×.

The results shown in FIG. 3 show that a PCR product has actually been amplified for the 3 genes of the arabinose pathway in all transformants tested (8). This finding suggests that these genes have been effectively integrated into the genome of the yeast.

In addition, a standard sequencing was carried out in order to check that the genes araA, B and D are not mutated (data not shown).

3. Selection of Strains Actually Capable of Metabolizing Arabinose:

In order to further pursue the investigations, it was chosen to simplify the system of expression of the arabinose pathway. To that effect, the cassette was modified to express genes ara A, B and D while being deprived of the coding sequence for an arabinose transporter (araT).

To measure the frequency of the appearance of strains that can metabolize arabinose, strain I-4953, registered at the CNCM on Jan. 29, 2015, was transformed using 1.3 µg of said cassette bearing araA, B and D.

The product of transformation was spread over 2 types of media:

A first medium corresponding to YPG (10 g/L of yeast extract; 10 g/L of peptone; 20 g/L of glucose as the sole source of carbon) containing Blasticidin in a quantity of 50 mg/L. The purpose is to determine the number of cells that have integrated the cassette into their genome;

A second medium called YNB-Ara corresponding to a minimal medium (YNB Difco®) containing 10 g/L of arabinose as the sole source of carbon. This medium must make it possible to determine the number of cells that have acquired the phenotype [ara+].

The YNB Difco® ("Yeast Nitrogen Base without amino acids and ammonium sulfate") medium, referenced under number 0335-15, contains:

Biotin 2 µg/L
Pantothenate (calcium) 400 µg/L
Folic acid 2 µg/L
Inositol 2000 µg/L
Niacin 400 µg/L
p-aminobenzoic acid 200 µg/L
Pyridoxine (chlorhydrate) 400 µg/L
Riboflavin 200 µg/L
Thiamin (chlorhydrate) 400 µg/L
Boric acid 500 µg/L
Copper sulfate 40 µg/L
Potassium Iodine 100 µg/L
Ferric chloride 200 µg/L
Magnesium sulfate 400 µg/L
Sodium molybdate 200 µg/L
Zinc sulfate 400 µg/L
Monobasic potassium phosphate 1 g/L
Magnesium sulfate 500 mg/L
Sodium chloride 100 mg/L
Calcium chloride 100 mg/L
Final pH=5.4
Ammonium Sulfate (5 g/L)

FIG. 4 illustrates the result obtained on both types of media.

After 6 days of growing in both media, the colonies were counted. It was observed that the number of colonies in the YNB-Ara medium was approximately 18% of that observed on the YPG+Blasticidin medium. In other words, only 18% of the colonies having integrated the genes araA, B and D in their genome seem able to grow by using arabinose as the sole carbon source.

It is clear from the foregoing that:

the cassette coding genes araA, B and D is necessary but not sufficient to obtain a phenotype [ara+];

the direct selection of transformants on a medium containing arabinose as the sole source of carbon is possible and in opposition to the teachings of Wisselink et al. (2007; Appl Environ Microbiol 73, 4881-4891), revealing that a prior step of growth in the presence of galactose is not necessary.

To continue, the cassette has been further simplified and deprived of any selection marker, notably resistance to antibiotics.

1156 transformants that grew on the YNB-Ara medium were then tested in Deep Well format (=microplate with 96 wells) to confirm their ability to grow anaerobically on arabinose and also to verify maintenance of their ability to ferment xylose and glucose.

The composition of the media used to this effect is detailed below:

YF Medium=
  Yeast extract (EXL) 5 g/L;
  Di-ammonium phosphate 4.7 g/L;
  Citric acid 11.4 g/L;
  Trisodium citrate 13.5 g/L;
  $ZnSO_4$ 21.2 mg/L;
  $MgSO_4$ $7H_2O$ 1 g/L;
  Thiamine 18.24 mg/L;
  Pyridoxine 5.28 mg/L;
  Biotin 1.76 g/L;
  Pantothenate 3.8 mg/L;
  Niacin 20 mg/L;
  Myo-inositol 50 mg/L;
  Riboflavin 1 mg/L;
  Para-aminobenzoate 1.2 mg/L;
  Tween 80, 1 g/L.
  Medium YF-ara: medium YF containing 70 g/L of arabinose
  Medium YF-xylose: medium YF containing 70 g/L of xylose The pH of the medium is kept at 5. The culture is carried out at 32° C.

FIG. 5 illustrates the results obtained with a series of strains whose growth was followed simultaneously on a medium containing arabinose (A) or xylose (B) as the sole source of carbon, the latter medium making it possible to select the strains that retained their ability to metabolize xylose.

The results shown in FIG. 5 show that the method of selecting strains [ara+] has still been improved: FIG. 5A shows that 15 of the 91 clones tested do not seem able to start multiplying again using arabinose. This would suggest that, as opposed to the selection based on resistance to an antibiotic, the selection on YNB-Ara makes it possible to obtain 85% of transformants that acquired the phenotype [ara+].

Another aspect that emerged from the results shown in FIG. 5 relates to the cohabitation of two metabolic pathways xylose and arabinose. It is thus apparent that certain strains have acquired the phenotype [ara+] to the detriment of phenotype [xyl+]. Others, on the other hand, have not retained the phenotype [ara+] after subculture on glucose (results not shown). However, of the 91 strains tested, 67 seem to have acquired and retained the double phenotype [ara+; xyl+], which is almost ¾ of the transformants.

4. Comparison Between 2 Selected Strains.
Fermentation on YFCF Medium:

The performance of 2 isolated clones (called clones 13 and 126, respectively) as described above were compared during fermentation in YFCF medium at pH 5 containing glucose as the carbon source, but also arabinose and xylose balance-represented, as well as acetic acid, thus approaching natural fermentation media.

More specifically, the composition of medium YFCF is as follows:
  10 g/L of yeast extract;
  10 g/L of bacto-peptone;
  63 g/L of glucose;
  28 g/L of xylose;
  28 g/L of arabinose;
  4 g/L of acetic acid (quantity added to the culture medium at pH 5).

Fermentation conditions are as follows:
  pH: 5
  Temperature: 32° C.
  02 conditions: without oxygen supply
  Agitation: 100 rpm
  Duration of culture: up to 72 hours
  Pre-Culture/Incubation: 0.25 g/kg eq DM of yeast previously propagated at saturation in YPG medium over 24 hours.

Ethanol production is measured indirectly by measuring the loss of mass from the fermentation flask, said mass loss correlating directly with $CO_2$ production, which is stoichiometric with that of alcohol. It is expressed in grams per kilogram of medium.

The concentrations of glucose, xylose, arabinose and glycerol in the medium are followed by HPLC.

Biomass variations are evaluated by measuring the residual dry material after 4 hours at 105° C.

The results shown in FIG. 6 reveal:
  a reduction in the speed of consumption of xylose for clone 13 compared to clone 126, also matched by a lower speed of ethanol production;
  it is notable that a rate of consumption of arabinose is slower in clone 13 than clone 126. Thus, after 32 hours of fermentation, clone 13 consumed 12.1+/−0.6 g/kg of arabinose, whereas clone 126 consumed 15.3+/−0.5 g/kg.

It is also noteworthy that the pentoses were consumed while the concentration of extracellular glucose was not null.

An attempt was made to explain the difference observed between clones 13 and 126, particularly the arabinose fermentation rate.

Analysis of Activities of the Pathway:

The intracellular enzyme activity involved in the metabolic pathways of arabinose and xylose were tested.

First, no notable difference was observed at the xylitol dehydrogenase activity level (results not shown).

On the other hand, a profile of arabinose isomerase activity (coded by araA) different between clones 13 and 126 was observed, with a more significant competitive inhibition for clone 13 (results not shown).

As shown in FIG. 7, this difference could be correlated with a difference in the level of reduction of the aldoses, more precisely the aldose reductase activity of both clones. Note that in the initial strain I-4953, the gene GRE3 coding the principal aldose reductase at S. cerevisiae was deleted, but residual activity remained (see FIG. 7).

Dosage of Aldose Reductase Activity in a Cell Extract:
Propagation of the Strains The strains to be tested were placed in a rich medium (YPG) to grow. Two successive propagation phases of 24 h at 30° C., under agitation, were required to obtain sufficient biomass. Once the biomass was harvested, the dry matter was measured on 1 ml of each cream after passing through the oven at 105° C. for 4 hours. The fermentations were carried out in 250 ml flasks containing 100 g of fermentation medium YF-xylose. Each flask was seeded at a rate of 0.5 g/kg equivalent dry matter. Fermentation proceeded at 32° C. under agitation at 110 rpm over 3 days. At that stage, 50 ml of fermentation product is collected and then serve to determine the different enzymatic activities and the protein concentration of the sample.

Preparing the Cell Extract 50 ml of fermentation product is collected by centrifugation (4700 rpm, 2 min, 4° C.) then resuspended in 3 ml of potassium phosphate buffer 0.1 M, pH 7. After another centrifugation, each pellet is then resuspended in 1 ml of potassium phosphate buffer 0.1 M, pH 7.

1 ml of resuspended pellet is then transferred to 1 tube for Fast Prep (filled earlier with 250 µl of balls) then crushed at 4° C.: 4×30 seconds (6 m/s), spaced at 30 seconds each. Next, the homogenate is centrifuged 3 minutes to 10000 rpm (to make the balls tumble along with the cell debris) and the totality of the supernatant is transferred to an Eppendorf tube cooled on ice.

Dosage of Enzyme Activities

Dosage of the enzyme activity is done by monitoring absorbance at 340 nm. Measurements are taken in a thermostatically-controlled environment at 32° C.

|  | white (µl) | sample (µl) |
|---|---|---|
| Phosphate buffer (KH2PO4/K2HPO4 0.1M pH = 7) pH = 7) | 750 | 750 |
| NAD (0.04M) |  | 100 |
| Cell extract |  | 20 |
| water | 750 | 430 (qs 1300) |
| xylitol 2M |  | 200 |

The substrate is added after 1 minute.

The results shown in FIG. 7 show a very sharp decline in aldose reductase activity in clones 13 and 126 compared to the parent strain I-4953. It is noted, however, that this activity is twice as high in clone 13 as in clone 126. This observation seems able to explain the poor performance of clone 13 compared to clone 126. To corroborate this result with the fermentation performances of xylose and/or arabinose, an attempt was made to increase the aldose reductase activity in clone 126.

Impact of Reintroducing a Gene Coding Aldose Reductase on the Ability of the Cells to Metabolize Arabinose:

There are two primary differences between clones 126 and 13 in their capacity to ferment xylose and arabinose and their capacity to reduce them into xylitol and arabitol, respectively. Insofar as these two phenotypes seem anti-correlated, an attempt was made to reinforce this activity in the cells of clone 126.

In that sense, the GRE3 gene that codes for the main aldose reductase on yeast *S. cerevisiae* (Garay-Arroyo and Covarrubias, 1999, Yeast 15, 879-892; Träff et al., 2001 Appl. Environ. Microbiol. 67, 5668-5674) was reintroduced. In practice, a copy of gene GRE3 placed under the dependence of the promoter of the ADH1 gene was integrated at the level of the native locus of GRE3 in the genome of clone 126.

In order to validate the good integration of the gene at the right locus, the following primers were used in the PRC reactions:

```
B6C2
(CCTATTGCTGTTTCCTCTTCAAAGTAC; SEQ ID NO: 7),
``` hybridizing in the terminator of the selection marker;

```
            B13B1 (T8),
                               (SEQ ID NO: 8)
            AGTTGTCAGTGCAATCCTTC;,
``` complementary to a region of the terminator of gene GRE3.

After verification of the integration of the cassette in the genome of the transformants selected (results not shown), their ability to use arabinose as the sole carbon source under anaerobic conditions was tested. In this sense, both the transformants and clone 126 were inoculated in an amount of 2 g (eq MS)/kg in YF-Ara medium.

The loss of mass after 48 hours of fermentation is shown in FIG. 8. These results show that all the clones having integrated the GRE3 gene have the capacity to ferment the arabinose that is diminished compared to clone 126. This result thus supports the hypothesis that a too strong aldose reductase activity limits the ability of the cells to ferment the arabinose.

Conclusions:

The integration of the arabinose fermentation pathway, i.e. of genes araA (*B. licheniformis*)/araB (*E. coli*)/araD (*E. coli*) at the level of the locus HO of strain I-4953 of *S. cerevisiae*, followed by a screening on a medium containing arabinose as sole source of carbon, made it possible to select strains capable of fermenting arabinose. In addition, it has been shown that among these strains, the most favorable were those that showed low aldose reductase activity. In this framework, a particularly interesting strain was isolated, namely strain EG31, and has been registered at the CNCM (Collection Nationale de Cultures de Microorganismes, Institut Pasteur, 25 rue du Docteur Roux, 75724 Paris Cedex 15) under number CNCM I-5085 on May 19, 2016.

II/ Obtaining a Strain of *Saccharomyces cerevisiae* Optimized for the Fermentation of Arabinose and Xylose:

1. Selection of a Strain Capable of Fermenting Arabinose and Xylose by Directed Evolution:

For the purpose of selecting a strain still optimized for the fermentation of pentoses, in particular arabinose, the strain EG31 was subjected to a directed evolution in batch.

Thus, a protocol for directed evolution making it possible to obtain the phenotype sought was perfected. For this, a medium has been defined and implemented in which the yeast that would consume only one of the two sugars would be disadvantaged. In practice, in the first medium named "GO xylose arabinose" and defined below, it is not the nitrogen source that is limiting, but the carbon sources. In practice, this medium contains 10 g/L of $(NH_4)_2PO_4$ but only 4 g/L of xylose and 5 g/L of arabinose.

Medium 1: GO Xylose Arabinose (pH 5):
Xylose 4 g/L
Arabinose 5 g/L
(NH4)2HPO4 (DAP) 10 g/L
Citric acid 11.4 g/L
Trisodium citrate 13.5 g/L
$ZnSO_4$ (0.004 g/L)
MgSO4 0.5 g/L
KH2PO4 1 g/L
NaCl 0.1 g/L
CaCl2 0.1 g/L
CuSO4 0.00006 g/L
H3B03 0.0005 g/L
KI 0.0001 g/L
MnSO4 0.0004 g/L
Na2MoO4 0.0002 g/L
FeCl3 0.0002 g/L
Pyridoxine 0.002 g/L
Biotin 0.0008 g/L
Pantothenate (0.002 g/L)
Nicotinic acid 0.001 g/L
Myo-inositol 0.001 g/L
Tween 80, 1 g/L The culture is done at 32° C. with stirring at 100 rpm in flasks stoppered by caps which serve to reduce the supply of oxygen in the medium and allow $CO_2$ which is produced throughout this culture in excess pressure to escape. Under these conditions, the culture lasts about seven days.

2. Selection of a Strain Having Retained its Ability to Ferment Glucose and/or Xylose in the Presence of Acetic Acid To anticipate a possible risk of loss of tolerance to inhibitors, particularly acetic acid in non-dissociated form, two successive cultures were introduced into the directed evolution cycle in batch into media containing either glucose or xylose as the sole carbon source, and in both cases in the presence of strong concentrations of acetic acid.

Medium 2: YF-Glucose Acid:

The YF-glucose acid medium corresponds to the YF medium described above, containing 150 g/L of glucose and presenting a concentration of acetic acid (quantity introduced into the culture medium at pH 4.4) equal to 5 g/L.

Medium 3: YF-Xylose Acid:

The YF-xylose acid medium corresponds to the YF-xylose medium described above, with a concentration of acetic acid (quantity introduced into the culture medium at pH 5) equal to 4 g/L.

Culture Conditions:

The culture is carried out at 32° C. with stirring at 100 rpm in flasks stoppered by caps which serve to reduce the supply of oxygen in the medium and allow the $CO_2$ in excess pressure that is produced throughout this culture to escape. Under these conditions, the culture lasts about seven days.

3. Elimination of "Petites":

To avoid selection of strains deprived of mitochondria, which would not be compatible with the industrial production processes, a step for culturing on a medium containing glycerol as the sole carbon source has also been added. This step requires the presence of a chain for the transfer of functional electron into cells so they can multiply.

Medium 4: YNB Glycerol:
- 3.4 g/L of DIFCO® nitrogen based yeast;
- 5 g/L of ammonium sulfate;
- 10 g/L of glycerol as the only carbon source.

The culture is done at 30° C. with stirring at 150 rpm in baffled flasks stoppered by porous caps which allow the supply of oxygen into the medium. Under these conditions, the culture lasts 24 to 48 hours.

In practice, a directed evolution cycle is characterized by:
- a culture on GO xylose arabinose medium; then
- a culture on YF glucose acid medium; then
- a culture on YF xylose acid medium; then
- a culture on YNB glycerol medium.

4. Evaluation of Clones so Obtained:

In practice, two cycles of culture were carried out.

At the end of this directed evolution, clones were individualized on dishes of complete medium, and the performances of the clones obtained were evaluated on a YFCF medium whose composition is given above. FIG. 9A shows the evolution of the production of ethanol as a function of fermentation time for 6 of the better clones obtained.

These results reveal that 5 out of 6 clones have a kinetic close to that of the EG31 strain, however with a final alcoholic titer greater than that of the EG31 strain. The last clone noted C7 seems more rapid during transition between the metabolism of sugars with 6 carbons to that of sugars with 5 carbons. Subsequently, the kinetics of fermentation seem to be the same as that of the other clones. At the end of fermentation, it seems that the alcoholic strength is greater with that strain than during implementation of the other clones.

To validate that this improvement is in fact related to a better consumption of arabinose, a dosage by HPLC was carried out to quantify the remaining sugars. FIG. 9B represents the concentrations of arabinose in the fermentation medium after 160 hours of fermentation. Results confirm that all the clones selected from the directed evolution consumed more arabinose than the EG31 strain, the clone noted C7 appearing to be the more efficient. This clone was renamed strain EG32, which was registered at registered at the CNCM (Collection Nationale de Cultures de Microorganismes, Institut Pasteur, 25 rue du Docteur Roux, 75724 Paris Cedex 15) under number CNCM I-5086 on May 19, 2016.

---

The invention claimed is:

1. A process for obtaining a yeast strain able to metabolize arabinose, glucose, and xylose in the presence of an organic acid in non-dissociated form, comprising:
   a integrating into the chromosome an L-arabinose isomerase gene (araA), an L-ribulokinase gene (araB) and an L-ribulose-5-P-4 epimerase gene (araD), in a yeast strain able to ferment xylose in the presence of an organic acid in non-dissociated form and having at least one aldose reductase (GRE3) gene inactivated or deleted;
   b directly putting the transformed strains into a medium containing arabinose as the sole carbon source, and culturing the strains in the medium for the selection of strains able to metabolize the arabinose, thereby obtaining yeast strains able to metabolize arabinose, glucose, and xylose in the presence of the organic acid;
   c optionally selecting transformed strains having metabolized arabinose for their aldose reductase activity less than or equal to 0.002 U/g protein, or even less than or equal to 0.0005 U/g of protein.

2. The process according to claim 1, wherein the yeast strain able to ferment xylose in the presence of an organic acid in non-dissociated form and having at least one GRE3 gene inactivated or deleted used is chosen from among *Saccharomyces, Schizosaccharomyces, Pichia, Yarrowia, Paffia, Kluyveromyces, Candida, Talaromyces, Brettanomyces, Pachysolen, Hansenula, Kloeckera, Schwanniomyces* and *Debaryomyces*.

3. The process according to claim 2, wherein the yeast strain able to ferment xylose in the presence of an organic acid in non-dissociated form and having at least one GRE3 gene inactivated or deleted is the strain registered at the CNCM on Jan. 29, 2015 under number I-4953.

4. A yeast strain obtained using the process according to claim 1, wherein the yeast strain further presents an aldose reductase activity less than or equal to 0.002 U/g of protein, or less than or equal to 0.0005 U/g of protein.

5. The yeast strain according to claim 4, wherein the yeast strain is strain I-5085, registered at the CNCM (Collection Nationale de Cultures de Microorganismes, Institut Pasteur, 25 rue du Docteur Roux, 75724 Paris Cedex 15) on May 19, 2016.

6. A process for obtaining a yeast strain with an improved ability to ferment arabinose, glucose and xylose in the presence of an organic acid in non-dissociated form, wherein the method comprises successively cultivating a yeast strain presenting a capacity to ferment arabinose, glucose, and xylose in the presence of an organic acid in non-dissociated form under the following conditions:
   a cultivating the yeast strain in an anaerobic or hypoxia culture in a medium containing, as sole carbon sources, arabinose and xylose in limiting concentrations for the production of biomass; then
   b performing two successive anaerobic or hypoxia cultures in the presence of an organic acid in non-dissociated form, one in a medium containing glucose as the sole carbon source and the other in a medium containing xylose as the sole carbon source; and
   c optionally cultivating the yeast strain in an aerobic culture in a minimum medium containing, as the sole carbon source, a source of strict respiratory carbon.

7. The process according to claim 6, wherein the successive steps (a) and (b) and, optionally, (c) are repeated at least 2 times.

8. A yeast strain obtained by the process according to claim 6, wherein the strain is strain I-5086, registered at the CNCM (Collection Nationale de Cultures de Microorganismes, Institut Pasteur, 25 rue du Docteur Roux, 75724 Paris Cedex 15) on May 19, 2016.

9. The yeast strain according to claim 4, wherein the yeast strain has at least one supernumerary copy of the HAA1 gene.

10. A yeast obtained by culture of a strain according to claim 4.

11. A process for the production of fermentation products or ethanol comprising the following steps:
    Incubation of a material or medium containing arabinose and/or xylose with a strain according to claim 4;
    Fermentation under anaerobic or semi-anaerobic conditions;
    Recovery of one or more fermentation product(s), or ethanol.

12. The process for production of fermentation products or ethanol according to claim 11, wherein the material or medium also contains glucose.

13. The process for production of fermentation products or ethanol according to claim 11, wherein the material or medium is hemicellulose or "corn fiber".

14. The process according to claim 6, wherein the organic acid in non-dissociated form is acetic acid.

15. The yeast strain according to claim 8, wherein the yeast strain has at least one supernumerary copy of the HAA1 gene.

16. A yeast obtained by culture of a strain according to claim 8.

17. The process for production of fermentation products or ethanol according to claim 11, wherein the strain is strain I-5086, registered at the CNCM (Collection Nationale de Cultures de Microorganismes, Institut Pasteur, 25 rue du Docteur Roux, 75724 Paris Cedex 15) on May 19, 2016.

18. The process for production of fermentation products or ethanol according to claim 17, wherein the material or medium also contains glucose.

19. The process for production of fermentation products or ethanol according to claim 18, wherein the material or medium is hemicellulose or "corn fiber".

20. The process for production of fermentation products or ethanol according to claim 12, wherein the material or medium is hemicellulose or "corn fiber".

* * * * *